US008241198B2

(12) United States Patent
Bull et al.

(10) Patent No.: US 8,241,198 B2
(45) Date of Patent: Aug. 14, 2012

(54) VENTRICULAR ASSIST DEVICE CAPABLE OF IMPLANTATION OF STEM CELLS

(75) Inventors: David A. Bull, Salt Lake City, UT (US); Rafe C. Connors, Bountiful, UT (US); Harold M. Erickson, Cora, WY (US); James Yockman, West Jordan, UT (US); Sung Wan Kim, Salt Lake City, UT (US)

(73) Assignee: University of Utah Foundation, Salt Lake City, UT (US)

( * ) Notice: Subject to any disclaimer, the term of this patent is extended or adjusted under 35 U.S.C. 154(b) by 455 days.

(21) Appl. No.: 12/513,310

(22) PCT Filed: Nov. 5, 2007

(86) PCT No.: PCT/US2007/023251
§ 371 (c)(1),
(2), (4) Date: Feb. 5, 2010

(87) PCT Pub. No.: WO2008/057481
PCT Pub. Date: May 15, 2008

(65) Prior Publication Data
US 2010/0145442 A1 Jun. 10, 2010

Related U.S. Application Data

(60) Provisional application No. 60/856,562, filed on Nov. 3, 2006.

(51) Int. Cl.
*A61M 1/12* (2006.01)
(52) U.S. Cl. .................. 600/16; 604/6.01; 604/6.09
(58) Field of Classification Search .................. None
See application file for complete search history.

(56) References Cited

U.S. PATENT DOCUMENTS

| 5,318,510 | A  | * | 6/1994  | Cathcart ................. 604/6.09 |
| 7,668,594 | B2 | * | 2/2010  | Brockway et al. ......... 607/9 |
| 7,828,711 | B2 | * | 11/2010 | Ross et al. ............. 600/17 |
| 2002/0182186 | A1 | * | 12/2002 | Loeb ................... 424/93.7 |
| 2010/0121391 | A1 | * | 5/2010  | Brockway et al. ......... 607/3 |

* cited by examiner

Primary Examiner — Kennedy Schaetzle
(74) Attorney, Agent, or Firm — Jackson Walker L.L.P.

(57) ABSTRACT

A biologic ventricular assist device that also has the capability to capture, grow, and administer stem cells to regenerate and restore damaged myocardium in the heart. The device works in conjunction with a traditional ventricular assist device and possesses an additional external path or tube that is in-line with the path of the ventricular assist device. The external path allows for the administration of stem cells, genes, genetically modified cells or other therapeutic biologic or pharmacologic agents, as well as leading to a stem cell collecting accessory (14) that captures circulating stem cells. The stem cell collecting accessory is also associated with a chamber (39) for culturing the captured stem cells. The cultured stem cells can be delivered back to the heart by an electro-mechanical or ultrasound/echocardiographic delivery system that runs through the external path back into the ventricular assist device and allows for the delivery of the stem cells, or other therapeutic biologic or pharmacologic agents, directly into the internal chambers of the heart. Administering the stem cells, genes, genetically modified cells or other therapeutic biologic or pharmacologic agents, either alone or in combination, to the heart allows the myocardium to regenerate and repair itself even while the heart is attached to the ventricular assist device, ultimately allowing the heart to regenerate, recover and allow the VAD to be removed.

5 Claims, 2 Drawing Sheets

VENTRICULAR ASSIST DEVICE CAPABLE OF IMPLANTATION OF STEM CELLS

BACKGROUND

This application claims priority to U.S. Provisional Patent Application Ser. No. 60/856,562, filed on Nov. 3, 2006, entitled VENTRICULAR ASSIST DEVICE CAPABLE OF IMPLANTATION OF STEM CELLS, the entire content of which is hereby incorporated by reference.

STATEMENT OF RIGHTS TO INVENTIONS MADE UNDER FEDERALLY SPONSORED RESEARCH

No federal funds were used in the development of the present invention.

This invention pertains to ventricular assist devices, and particularly to a ventricular assist device that can support a heart either through culture and/or therapeutic external administration of stem cells.

Aging of the population and prolongation of the lives of cardiac patients by modern therapeutic innovations has led to an increasing prevalence of heart failure ("HF"). Despite improvements in both medical and surgical therapy, the mortality rate in patients with HF has remained unacceptably high.

The surgical management of patients with end-stage heart failure is slowly evolving. Heart transplantation remains the ultimate treatment for heart failure, but the persistent shortage of donor hearts continues to limit the annual growth of this approach. Thus, heart transplantation is not an available option for most patients with HF and continues to be performed only at large, highly specialized medical centers. Ventricular assist devices ("VADs") are currently most commonly used as a bridge to transplantation, but are now being designed as destination therapy for many HF patients.

Studies have been completed showing the beneficial effect of gene therapy for myocardial neovascularization. Animal studies show evidence of cardiac progenitor cells, or cardiac stem cells, existing in the atria and ventricles. These cells have been harvested from myocardium of several different vertebrate species and subsequently grown in vitro. These same types of cells exist in human myocardium.

The current state of the art therapy is in evolution. VADs are coming to the forefront of therapy with cardiac transplantation. However, at the present time, VADs can only support a patient in cardiogenic shock until a donor heart becomes available for transplant. The current generation of VADs do nothing to help regenerate the heart to restore it to a normal level of functioning. Indeed, research demonstrates that the longer a ventricular assist device is in place, the more likely it is that the heart muscle will be replaced by scar tissue, resulting in an atrophic, non-functioning heart, incapable of functioning without the VAD in place. In addition, a few centers have gained FDA approval to begin Phase I human clinical trials with bone marrow mononuclear cells as therapy for myocardial ischemia. While bone marrow mononuclear cell therapy holds significant promise for therapy, early long-term data indicates that the bone marrow-derived cells do not differentiate into mature myocytes or blood vessels.

What is needed, therefore, is a therapy for HF patients that can support a patient in end-stage heart failure, such as a VAD, and that can utilize other biologic and/or pharmacologic therapies to regenerate the heart and help restore it to a normal level of functioning.

SUMMARY

The present invention relates generally to the field of ventricular assist devices. In particular, this invention relates to a biologic ventricular assist device that also has the capability to capture, grow, and administer stem cells, other therapeutic biologic agents and other therapeutic pharmacologic agents, either alone or in combination, to regenerate and restore damaged myocardium in the heart.

Native progenitor or stem cells which are capable of repairing and regenerating the organs of the human body offer a novel means to address the problem of myocardial atrophy with the VAD in place. These progenitor or stem cells are routinely present both within solid organs and circulating in the blood stream. The advantage of the cardiac progenitor cells is that they are already resident within the myocardium and have demonstrated in other animal studies to differentiate only into cardiac myocytes, coronary arterioles, and capillary structures, and are already believed to do so within the myocardium during ischemic periods. Unfortunately, their numbers at any given time are so small that these cells have not been thought to be a practical means of externally directing large scale tissue regeneration or repair. The current biologic ventricular assist device allows for the capture, growth, and administration of therapeutic biologic or pharmacologic entities which include but are not limited to: cells, stem cells, genes, genetically modified and/or cultured stem cells, drugs, and components of the extracellular matrix either alone or in combination, to allow them to be applied in a truly therapeutic fashion to regenerate and restore damaged myocardium.

The biologic ventricular assist device, BIOVAD™ (any ventricular assist device that allows for the capture, growth, and administration of therapeutic biologic or pharmacologic entities including but not limited to: cells, stem cells, genes, genetically modified and/or cultured stem cells, drugs, and components of the extracellular matrix either alone or in combination), offers a novel means to regenerate and restore the native heart while the VAD is in place, with the ultimate goal of allowing the removal of the VAD and obviating the need for a heart transplant. The biologic ventricular assist device does this by using the native cardiac progenitor cells isolated at the time that the VAD is placed, growing them to confluence either within or outside the body, then re-administering them to the patient via an electro-mechanical and/or ultrasound/echocardiographic imaging delivery system which allows electro-mechanical echocardiographic imaging of the heart, such as a NOGA catheter system. This electro-mechanical and/or ultrasound/echocardiographic imaging and delivery system will pass through an external sleeve system placed along the drive line and along the course of the device back into the internal cardiac chambers to allow the delivery of the appropriate dose of cardiac progenitor or stem cells. This external to internal sleeve system allows for repeated delivery of therapeutic biologic or pharmacologic entities including but not limited to: cells, stem cells, genes, genetically modified and/or cultured stem cells, drugs, and components of the extracellular matrix, either alone or in combination, to the native myocardium over time, allowing the heart to repair itself in a graded, step-wise, physiologic fashion.

The tissue obtained during VAD placement is usually discarded following surgery. During cannulation of the atrium prior to going on cardiopulmonary bypass, a small and inconsequential piece of atrium can be obtained from the cannulation site. Further, the ventricular apex is cored out for placement of the device. This section of the wall of the apex of the left ventricle and/or the resected portion of the atrium are used as the source of cardiac progenitor and stem cells resident in the myocardium. These cells can be isolated and grown externally to supply the cardiac stem cells for later re-administration.

The biologic ventricular assist device also utilizes an in-line chamber to capture circulating stem cells which are normally in small numbers in circulation, grow them up to a critical mass or density at which they become therapeutic using a "bio-reactor" within the chamber, and then return them to the damaged heart either in an internal automated or external selectively determined fashion to repair and restore the damaged heart. This ultimately allows for the removal of the ventricular assist device. The principle of the biologic ventricular assist device is that a chamber is placed in-line with the circuit through which blood flows. This in-line chamber contains a series of polymeric filters embedded with chemokines and cytokines which serve to attract and capture stem cells which are circulating in very low numbers in the blood stream. The chamber also contains nutrient elements which allow the stem cells to proliferate in a contained "bio-reactor." Once the cells reach confluence, they can be removed to allow genetic modification prior to re-administration or they can be returned directly back to the heart to help regenerate viable heart tissue and ultimately restore a heart which is capable of supporting its own function sufficiently to allow the VAD to be removed.

The chamber to capture circulating stem cells and allow their proliferation within a bioreactor is adaptable to any in-line blood circuit with any connection to the bloodstream. The most obvious related extensions of this technology would be to patients undergoing dialysis, plasmapheresis, or any clinical setting in which a chamber system can be placed in-line to capture circulating cellular elements within the blood.

DETAILED DESCRIPTION OF PREFERRED EMBODIMENTS

Figure 1:
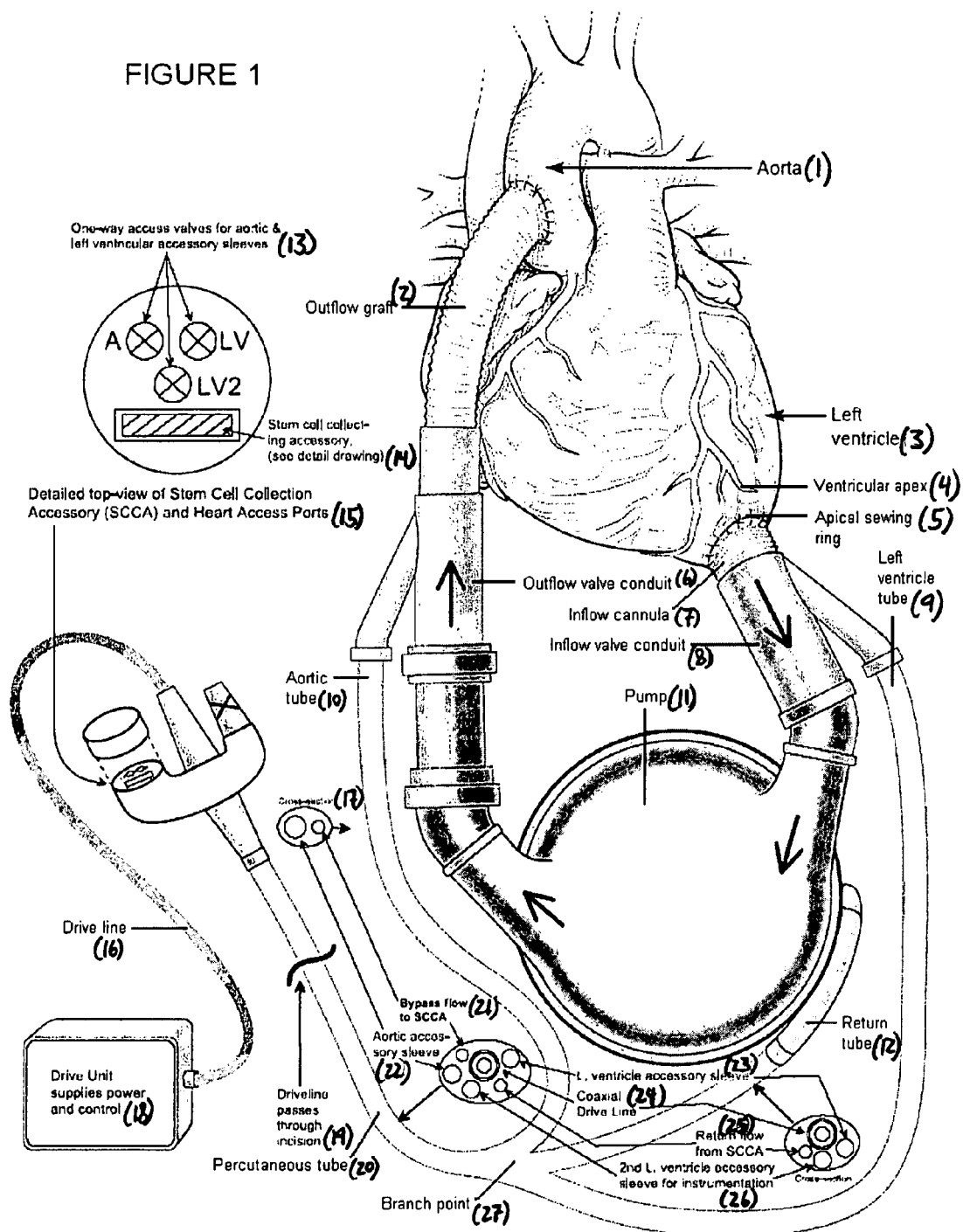
FIG. 1 shows a schematic of one embodiment of the biologic ventricular assist device.

One aspect of the present invention pertains to a biologic ventricular assist device (FIG. 1) that is capable of capturing, culturing, and delivering stem cells within a heart to which the device is attached. The ventricular assist device includes an inflow path (7,8), a pump (11), and an outflow path (6,2). The inflow path (7,8) of the ventricular assist device is attached to the left ventricle of the heart (3), and blood flows into the inflow path (7,8) from the left ventricle (3). The inflow path (7,8) then passes into the pump (11), which directs the blood into the outflow path (6,2). The outflow path directs the blood back into the ascending aorta of the heart (1). A drive line (16) typically connects the pump to a drive unit (18) that is external to the body. In the current invention, an external path is also attached at various points to the inflow path (7,8), the pump (11), and the outflow path (6,2) of the ventricular assist device (FIG. 1). Blood also flows through the external path. The external path leads to a stem cell collection accessory ("SCCA", FIG. 2) which captures circulating stem cells in the blood or from the heart.

Another aspect of the present invention is the stem cell collection accessory ("SCCA", FIG. 2), which is a path or chamber through which blood flows after it is directed there by the external path. The path or chamber has walls of selective permeability and one or more layers of gels or polymers (36, 35, 33, 31, 34) having a chemical gradient sufficient to cause migration of the stem cells from the blood through the walls and into the surrounding gel.

In the present invention, once the captured stem cells are grown to confluence, the stem cells are re-suspended and delivered back to the internal chambers of the heart using a delivery system that also passes through the external path. This external path leading back to the heart allows for repeated delivery of not only the captured and cultured stem cells but also therapeutic biologic or pharmacologic entities including but not limited to: cells, stem cells, genes, genetically modified and/or cultured stem cells and drugs, either alone or in combination, over time.

In a preferred embodiment, an inflow cannula (7) and inflow valve conduit (8) passing out of the left ventricle of the heart (3) make up the inflow path of the biologic ventricular assist device (FIG. 1). The inflow path (7,8) directs the blood into the pump (11), which then directs the blood into the outflow path (6,2). In a preferred embodiment, an outflow valve conduit (6) and outflow graft (2) make up the outflow path. In an additional preferred embodiment, the external path of the biologic ventricular assist device is made up of a left ventricle tube (9), an aortic tube (10), a percutaneous tube (20), and a return tube (12).

FIG. 1 shows one preferred embodiment of the biologic ventricular assist device. The heart is illustrated, including the left ventricle (3) and aorta (1). Positioned at the ventricular apex (4) is an apical sewing ring (5) that allows attachment of the inflow cannula (7) of the device. The inflow cannula (7) passes into the inflow valve conduit (8), allowing blood exiting the left ventricle (3) to flow into the pump (11). Also exiting the inflow valve conduit (8) is a left ventricle tube (9) through which blood can bypass the pump (11) and proceed in a direction toward the stem cell collection accessory ("SCCA", FIG. 2). The left ventricle tube (9) can also contain one or more accessory sleeves (23) or lines for instrumentation (26). In a preferred embodiment, these accessory sleeves can be called left ventricle accessory sleeves (23). The tube may be attached at the inflow valve conduit (8) with one-way valves for the accessory sleeves (23) and open ports for the lines involved with blood flow.

At a branch point (27), the left ventricle tube (9) merges into a percutaneous tube (20) leading out of the body, past the incision and out of the skin, with a drive line (16) leading eventually back to the drive unit (18). Also at this branch point (27), an aortic tube (10) enters the percutaneous tube (20) from a point at the outflow valve conduit (6). The aortic tube (10) may contain one or more accessory sleeves (22) or lines allowing for the bypass flow of blood directly out of the outflow valve conduit and the aorta (21) toward the stem cell collection accessory ("SCCA"). In a preferred embodiment, these may be called an aortic accessory sleeve (22) and a bypass flow line (21). The aortic tube (10) may be attached at the outflow valve conduit (6) with one-way valves for the accessory sleeves and open ports for the lines involved with bypass blood flow. The percutaneous tube (20) also contains the accessory sleeves and lines allowing for ex-vivo delivery of therapeutic biologic or pharmacologic entities including but not limited to: cells, stem cells, genes, genetically modified and/or cultured stem cells, drugs, and components of the extracellular matrix, either alone or in combination, within the other tubes, as well as the coaxial drive line that runs between the drive unit (18) and the pump (11). Blood exiting the pump (11) that is not involved in bypass flow passes through the outflow valve conduit (6) and through the outflow graft back (2) into the ascending aorta (1).

Also entering the percutaneous tube (20) at the branch point (27) is a return tube (12) that can return blood to the pump (11) after it passes out of the stem cell collection accessory ("SCCA", FIG. 2) and through the percutaneous tube (20). The return tube (12) can also contain one or more accessory sleeves (23, 26) or lines allowing for ex-vivo delivery of therapeutic biologic or pharmacologic entities including but not limited to: cells, stem cells, genes, genetically modified and/or cultured stem cells, drugs, and components of the extracellular matrix, either alone or in combination, as well as accessory sleeves or lines allowing for instrumentation. Where the return tube (12) meets the pump (11), a drive line (16) may also enter the tube for passage back to the drive unit (18). These accessory sleeves or lines may be called in a preferred embodiment left ventricle accessory sleeves (23), and a return flow line (25).

The percutaneous tube (20) passes outside of the body at the skin line and enters an adapter containing a vent filter, a stem cell collection accessory ("SCCA", FIG. 2), and one-way access valves for access to the aortic accessory sleeve, the left ventricle accessory sleeve, and the second left ventricle accessory sleeve (13). The drive line (16) can continue past the adapter to the drive unit (18).

Figure 2:
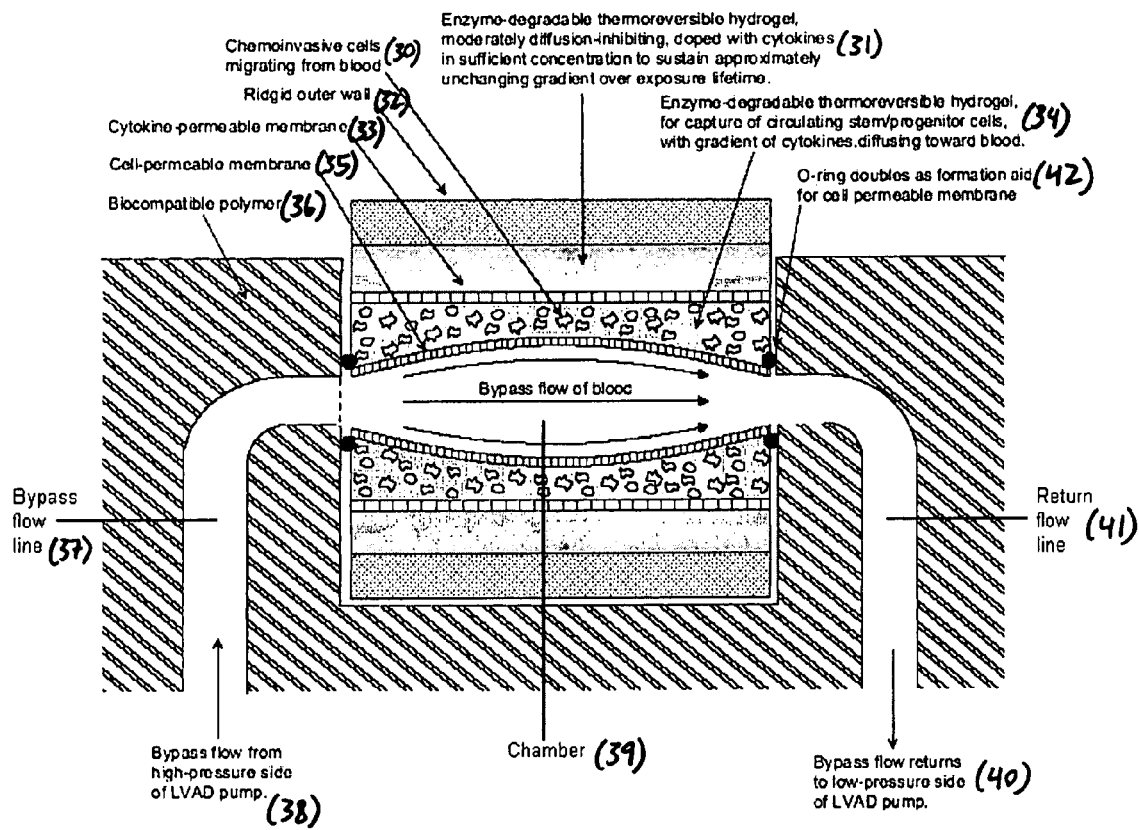
FIG. 2 shows an schematic of one embodiment of the stem cell collection accessory.

FIG. 2 shows an illustration of a preferred embodiment of a stem cell collecting accessory. Blood enters the stem cell collecting accessory from the bypass flow line (37). The bypass flow line (37) contains blood that passed through the pump (11), exited at the outflow valve conduit (6), passed through the aortic tube (10), passed into the percutaneous tube (20) at the branch point (27), and entered the adapter. This blood flow comes from the high pressure side of the device. The stem cell collecting accessory (FIG. 2) is generally surrounded by a biocompatible polymer (36). Within the stem cell collecting accessory itself is a chamber (39) through which blood passes. O-rings (42) may be located at either end of the chamber. The first layer surrounding the chamber is a cell-permeable membrane (35). The O-rings (42) also serve as formation aids for this cell-permeable membrane. Outside of the cell-permeable membrane (35) is an inner enzyme-degradable thermoreversible hydrogel (34) which contains a gradient of cytokines diffusing toward the flow of blood. The gradient in this hydrogel serves to capture circulating progenitor or stem cells as they migrate through the cell-permeable membrane. Chemoinvasive cells (30) migrate into this hydrogel from the blood. Outside the hydrogel is a cytokine-permeable membrane (33) through which the stem cells do not easily pass. Outside of the cytokine-permeable membrane (33) is an outer enzyme-degradable thermoreversible hydrogel (31) that is doped with cytokines in sufficient concentration to sustain an approximately unchanging gradient over the exposure lifetime. This outer hydrogel is moderately diffusion-inhibiting. The outermost layer is a rigid outer wall (32).

The blood that flows through the stem cell collecting accessory (FIG. 2) then enters the return flow line (25). The return flow line (25) passes through the percutaneous tube (20), passes into the return tube (12) or any line allowing for the return flow of blood at the branch point (27), and re-enters the pump (11). This blood flow is directed to the low pressure side of the device.

Once they have grown to confluence within the stem cell collection assembly, the cardiac or circulating progenitor or stem cells are removed from the stem cell collecting accessory, re-suspended in solution and then re-administered via the electro-mechanical and/or ultrasound/echocardiographic imaging and delivery system directed through the external sleeve system within the percutaneous tube and other tubes placed along the drive line and along the course of the device back into the internal cardiac chambers to allow the delivery of the appropriate dose of cardiac progenitor or stem cells.

EXAMPLE 1

Cardiac Progenitor Cell Isolation

Isolation and Characterization of Cardiac Stem Cells. Tissue samples are obtained from patients receiving a left ventricular assist device (LVAD). The 1-2 $cm^3$ samples are excised from the left ventricular apex to allow for placement of the device. Typically, this "core" is discarded upon excision. However, this is a viable source of tissue, regardless of the pathological background, to isolate resident cardiac stem cells.

Processing of Human Cardiac Stem Cells from Clinical Samples. The cardiac tissue "core" is minced with a scalpel into 2-3 $mm^3$ pieces, and 20 pieces (generally, 500 mg) are placed into 2 ml of 0.13 mg/ml Liberase Blendzyme 4 (Roche Diagnostics Corp., San Diego, Calif.) re-suspended in serum free Hams F12 media. The tissues are incubated for 30 minutes with a brief vortexing every 10 minutes. The larger tissues are collected by centrifugation at 500 R PM for 2 minutes and the supernatant collected and strained through a 30 uM nylon mesh. The remaining tissue is re-suspended in 2 ml of 0.13 mg/ml Liberase Blendzyme 4 and the procedure is repeated for a total of three times. Each time the supernatant is collected, the sample is strained through the nylon mesh and the cells spun at 800 RPM for 10 minutes to pellet the cells. These cells are re-suspended in calcium and magnesium free PBS supplemented with 0.1% BSA (Sigma, St. Louis, Mo.) and 2 mM EDTA and placed in the incubator until all sample digestions have been completed. Following digestion, the cells will be pooled and counted on a hemacytometer. Viability will be measured by trypan blue exclusion.

Magnetic isolation of $CD117^{pos}/Pgp^{pos}$ stem cells. $CD117^{pos}/Pgp^{pos}$ (P-glycoprotein) cells are labeled with 1 µg of biotinylated mouse anti-human CD117 (eBioscience, San Diego, Calif.) and biotinylated mouse anti-Pgp (Chemicon, Temecula, Calif.) per $1 \times 10^7$ cells for 30 minutes at 4° C. Following incubation, the cells are washed in PBS plus 0.1% BSA and 2 mM EDTA and re-suspended in $2 \times 10^7$ cells/ml of wash buffer. A total of 25 µl of Streptavidin coated CELLection Dynabeads® (Dynal®, Invitrogen, Carlsbad, Calif.) is added to the cells and incubated with gentle tilting and rotation for 30 minutes. The cells are placed into the Dynal® MPC-L magnet for 2 minutes. The supernatant is removed and the bead bound cells are washed 3 times in wash buffer. The supernatant is collected and stored separately. The bead bound cells are re-suspended in 200 µl of RPMI 1640 plus 1% FBS and 4 µl of 10,000 U/ml DNaseI is added for 15 minutes with gentle tilting and rotation. The sample is then vortexed vigorously and placed into the magnet for 2 minutes. The supernatant is then collected and the tube washed once in RPMI 1640 plus 1% FBS. The supernatant is pelleted at 800 RPM for 10 minutes and re-suspended in growth media, Ham's F12 supplemented with 5% FBS and 10 ng/ml each of LIF (Chemicon) and bFGF (Chemicon). The cells are counted on a hemacytometer and plated in a 6-well plate (Nunc, Rochester, N.Y.) at $2 \times 10^4$ cells/$cm^2$. The supernatant is replaced after one week and the plate washed with PBS and maintenance media is added, Ham's F12 supplemented with 5% FBS, 10 ng/ml LIF and bFGF and 20 ng/ml of EGF (Chemicon). Media is changed every 3-4 days until 50% confluency. Upon 50% confluency, the plate is passaged into a 75 cm² flask (Nunc). The negatively sorted cells are plated at a density of 5×10⁵ cells/cm² on 75 cm² flasks in growth media (described in D.1.2.). These cells are treated similarly to positive selected cells in regards to media and passaging. Yield, morphology, homogeneity, and cell growth characteristics are documented for each sample and their isolates.

Adherent isolation of cardiac stem cells. Cells processed from clinical cardiac samples are plated at a density of 5×10⁵ cells/cm² on 75 cm² flasks in growth media. Adherent and non-adherent fractions are collected based on the following time points: 1 hour, 2 days, 5 days and 7 days. The adherent fractions then have the media replaced with maintenance media. The supernatant containing the non-adherent cells, is pelleted and re-suspended in maintenance media and plated on 75 cm² flasks. Once 50% confluence is reached, the cells are passaged to 175 cm² flasks in maintenance media. Yield, morphology, homogeneity, and cell growth characteristics are documented for each sample and their isolates.

Flow cytometry characterization. Cells are characterized through flow cytometry for phenotypic surface markers to determine the efficacy and homogeneity of the isolation techniques. Cells are stained, with mouse anti-human antibodies (Pharmingen, BD Biosciences, Mississauga, Canada) for stem cell markers CD105, CD117, CD133, CD166, the drug resistance marker, P-glycoprotein (Pgp), as well as lineage markers, CD4, CD8, CD20, CD34, CD45, CD45RO and the endothelial marker CD31 and adhesion marker CD44. Cells are trypsinized with TrypLE (Invitrogen), pelleted, and re-suspended in PBS plus 5% BSA at a density of 1×10⁶ cells/ml. 200 µl of the cells are aliquoted into 12×75 mm tubes and 0.5 µg of appropriate antibodies are added to each tube. Four different antibodies are added per tube that possess particular fluorescent characteristics so that there is little fluorescent emission overlap. The antibodies are incubated at 4° C. for 30 minutes, washed in PBS plus 5% BSA and re-suspended in 1 ml PBS. Cells are analyzed using the Becton Dickinson FAC-Scan Analyzer and CellQuest software (Becton-Dickinson, BD Biosciences).

Differentiation capacity of cardiac stem cells. Cells are trypsinized and placed onto a Nunc eight-well LabTek™ chamber slides (Sigma) at 1×10³ cells/cm² and grown under normal or differentiative conditions. Media are changed every 3-4 days. The number of positive cells are counted using a fluorescent microscope and representative micrographs are taken with the Olympus BX50WI (Center Valley, Pa.) two photon confocal microscope available. Background staining consists of Prolong Gold™ anti-fade plus DAPI (Molecular Probes, Invitrogen).

Cardiomyogenic differentiation of stem cells following co-culture with neonatal cardiomyocytes. To induce cardiomyogenic differentiation, human cardiac stem cells ("hCSC's") are co-cultured with neonatal human ventricular myocytes ("NRVMs"). CSCs are labeled with PKH-26 (Sigma) prior to addition to the NRVMs cultures at a 1:4 ratio and cultured for up to 2 weeks with media changes every 3-4 days. PKH-26 labeled cells retain both biological and proliferative activity, and are ideal for cell tracking studies. The linkers are physiologically stable (lasting up to 100 days) and show little to no toxic side effects. PKH-26 has an excitation and emission of 551/567 nm that is compatible with rhodamine or phycoerythrin detection systems. However, it may also be excited by the 488 nm emission of an argon-ion laser. Briefly, cells are trypsinized from the plate, pelleted and washed twice in serum-free media. After the final wash, the cells are suspended at 4×10⁵ in 50 µl diluent. 50 µl of 2×PKH-26 dye is added and the cells are incubated at room temperature for approximately 5 minutes. This time may change as each cell type exhibits different properties in lipid uptake. To ensure homogenous staining, cells are incubated for different times and analyzed by confocal microscopy. The reaction is stopped by adding an equal amount of growth media with FBS and the cells are washed 3-5 times to remove any unbound dye. Cells are stained for rabbit anti-human cardiac troponin I (Abcam, Cambridge, UK), biotinylated goat anti-human GATA-4 and mouse anti-human Nkx2.5 (R&DSystems, Minneapolis, Minn.).

Endothelial differentiation of stem cells. To induce differentiation into endothelial cells, hCSCs are plated at 5×10⁴/cm² in DMEM or EBM-2 (Cambrex) with 2% FBS, supplemented with 10⁻⁸ M dexamethasone and 10 ng/ml VEGF, in chamber slides coated with either 0.1% gelatin or fibronectin for 14 days with media changes every 3-4 days. Tube-like structures may form after five days, but after 14 days they exhibit endothelial specific markers. Cells are stained for rabbit anti-human von Willebrands Factor ("vWF"), and mouse anti-human CD31.

Smooth muscle differentiation. Cardiac stem cells and MSCs are induced to differentiate into smooth muscle cells by placing 5×10⁴/cm² stem cells on fibronectin coated glass chamber slides in 2% DMEM or EBM-2 (Cambrex) supplemented with 50 ng/ml PDGF-BB for 14 days. The SMC marker, mouse anti-human alpha-smooth muscle actin (Abcam), is used.

What is claimed is:

1. A biologic ventricular assist device capable of capturing, culturing, and delivering therapeutic biologic or pharmacologic entities, either alone or in combination, within a heart to which the device is attached, comprising:
   a ventricular assist device comprising an inflow path, a pump, and an outflow path, through which blood flows; and
   a stem cell collection accessory attached on an external path to the inflow path, the outflow path, and the pump of the ventricular assist device, through which blood flows, for capturing circulating therapeutic, biologic or pharmacologic entities in the blood or from the heart.

2. The biologic ventricular assist device of claim 1, further comprising a chamber connected to the stem cell collection accessory for culturing the captured stem cells.

3. The biologic ventricular assist device of claim 2, further comprising an electro-mechanical or ultrasound/echocardiographic delivery system connected to the chamber, the inflow path, the outflow path, and the external path for delivery of the stem cells as well as other therapeutic biologic or pharmacologic entities including other cells, stem cells, genes, genetically modified and/or cultured stem cells, drugs, and components of the extracellular matrix, or any combination thereof, either alone or in combination, in polymer or other bioengineered delivery vehicles to the heart.

4. The biologic ventricular assist device of claim 1, wherein the inflow path is adapted to be attached to the left ventricle of the heart and the outflow path is attached to the ascending aorta of the heart.

5. The biologic ventricular assist device of claim 1, wherein the stem cell collection accessory comprises a path through which the blood flows having walls of selective permeability and a surrounding gel having a chemical gradient sufficient to cause migration of stem cells from the blood through the walls and into the surrounding gel.

* * * * *